US00PP35261P2

(12) United States Plant Patent
MacGregor et al.

(10) Patent No.: US PP35,261 P2
(45) Date of Patent: Jul. 11, 2023

(54) ***ANEMONE* PLANT NAMED 'MACANE044'**

(50) Latin Name: ***Anemone* L.**
Varietal Denomination: MACANE044

(71) Applicants: Alasdair MacGregor, Kirkcudbright (GB); Elizabeth MacGregor, Kirkcudbright (GB)

(72) Inventors: Alasdair MacGregor, Kirkcudbright (GB); Elizabeth MacGregor, Kirkcudbright (GB)

( * ) Notice: Subject to any disclaimer, the term of this patent is extended or adjusted under 35 U.S.C. 154(b) by 0 days.

(21) Appl. No.: 17/803,884

(22) Filed: Jan. 9, 2023

(51) Int. Cl.
*A01H 5/02* (2018.01)
*A01H 6/72* (2018.01)

(52) U.S. Cl.
USPC ..... Plt./263.1
CPC ..... *A01H 6/72* (2018.05)

(58) Field of Classification Search
USPC ..... Plt./263.1
CPC ..... A01H 6/72; A01H 5/02
See application file for complete search history.

*Primary Examiner* — Keith O. Robinson
(74) *Attorney, Agent, or Firm* — Samuel R. McCoy, Jr.

(57) ABSTRACT

'MACANE044' is a new and distinctive *Anemone* plant which is characterized by a clumping growth habit with flowers born relatively high above the foliage, flowers with tepals arranged in two whorls, tepals with an upper surface that is white and heavily suffused with violet, proximal tepals with a lower surface that is partially or entirely colored purple, and a long flowering season. The new variety propagates successfully by stem cuttings and has shown to be uniform and stable in the resulting generations from asexual propagation.

2 Drawing Sheets

Latin name of the genus and species: The Latin name of the genus and species of the novel variety disclosed herein is *Anemone* L.

Variety denomination: The inventive variety of *Anemone* disclosed herein has been given the variety denomination 'MACANE044'.

CROSS REFERENCE TO RELATED APPLICATIONS

This application claims priority to the Community Plant Variety Rights application number 2022/0056, filed Jan. 11, 2022, which is herein incorporated by reference.

BACKGROUND OF THE INVENTION

Parentage: 'MACANE044' is the result of a controlled cross-pollination breeding program carried out by the inventors at their commercial nursery in Kirkcudbright, Scotland, in the summer of 2015. The inventors began by performing a controlled cross-pollination of *Anemone* 'Rosenschale' (unpatented), the seed parent, with an unnamed *Anemone* plant (unpatented), the pollen parent. Seed from said cross was harvested, then germinated, and the resulting seedlings were then grown to a mature size in order to evaluate for desirable commercial characteristics. In the summer of 2016, the inventors selected the new *Anemone* plant due to its unique flower and bloom characteristics. This new and distinctive cultivar was given the name 'MACANE044'.

Asexual Reproduction: Asexual reproduction of 'MACANE044' was first accomplished in the winter of 2016 by way of root cuttings at the inventor's nursery in Kirkcudbright, Scotland. Four successive generations have shown that the unique features of the instant plant are stable and reproduce true to type.

SUMMARY OF THE INVENTION

The cultivar 'MACANE044' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Anemone* plant, 'MACANE044'. These traits, in combination, distinguish 'MACANE044' as a new and distinct cultivar.

1. *Anemone* 'MACANE044' exhibits a clumping growth habit with flowers born relatively high above the foliage; and
2. *Anemone* 'MACANE044' exhibits flowers with tepals arranged in two whorls; and
3. *Anemone* 'MACANE044' exhibits tepals with an upper surface that is white and heavily suffused with violet, particularly in the central zone of the tepals; and
4. *Anemone* 'MACANE044' exhibits proximal tepals with a lower surface that is partially or entirely colored purple; and
5. *Anemone* 'MACANE044' exhibits a long flowering season, from summer through late summer when grown in Kirkcudbright, Scotland.

BOTANICAL DESCRIPTION OF THE PLANT

Figure 1:
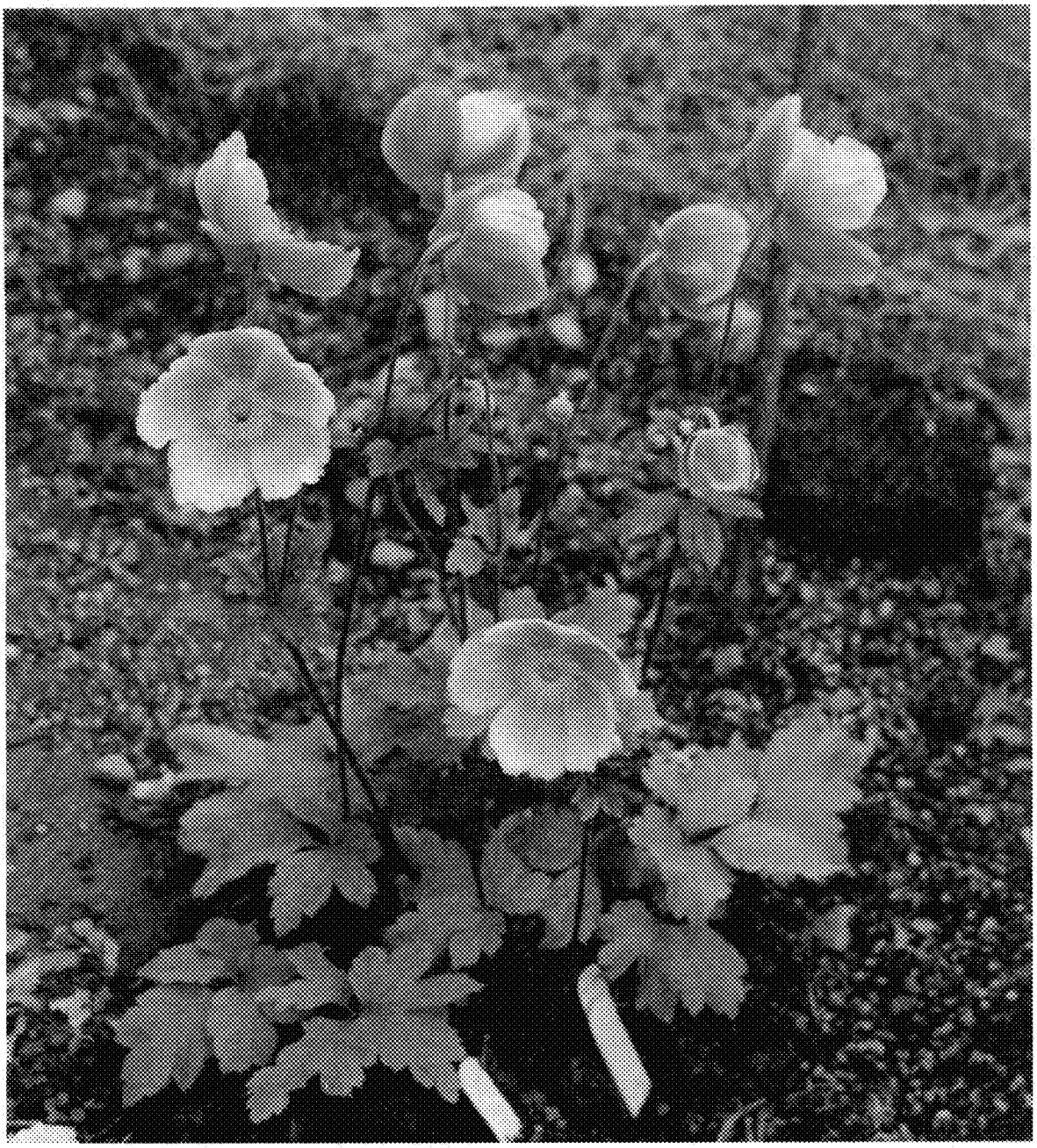
FIG. 1 shows, as nearly true as it is reasonably possible to make the same in color illustrations of this type, the typical foliage and growth characteristics of the new cultivar, 'MACANE044'. The plant shown is approximately 12 to 15 months old.
Figure 2:
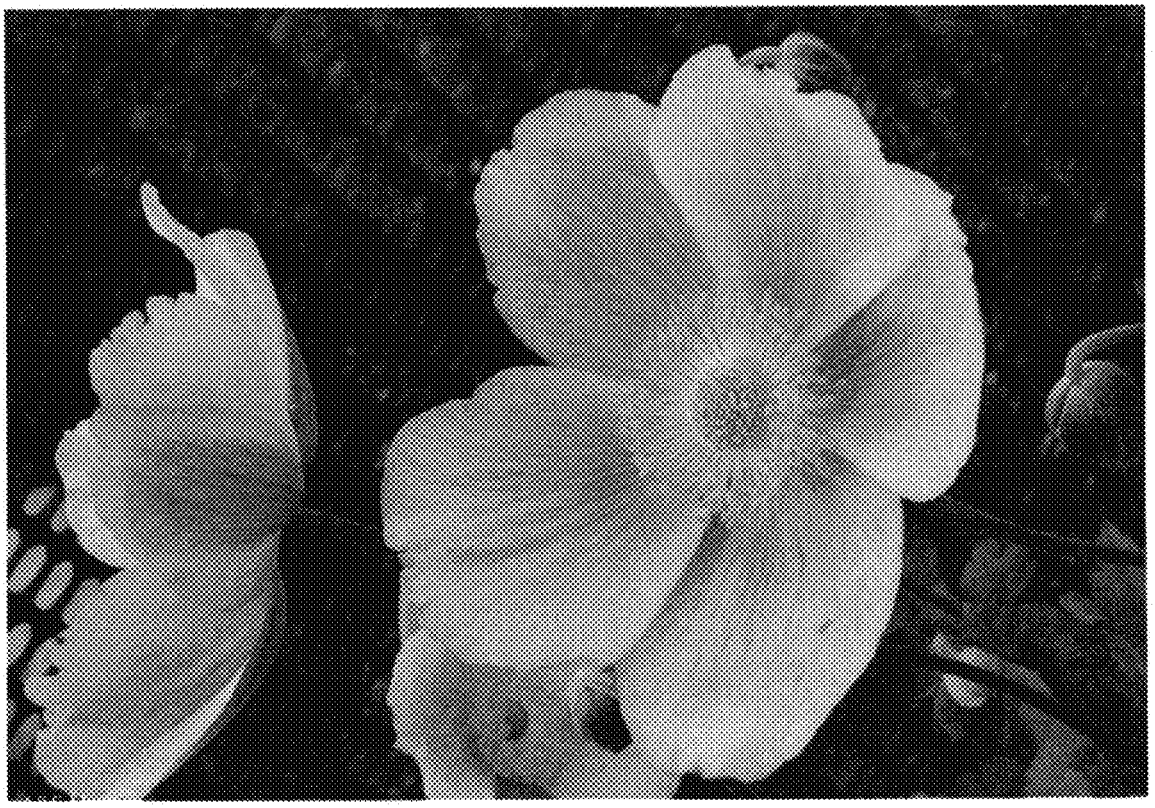
FIG. 2 shows, as nearly true as it is reasonably possible to make the same in color illustrations of this type, the typical flower of the plant in FIG. 1.

The following is a detailed botanical description of a new and distinct variety of *Anemone* hybrid known as 'MACANE044', based upon observations of field-grown plants, approximately 12 to 15 months old, grown at a commercial nursery in Kirkcudbright, Scotland. Plants were grown in full sun to partial shade using accepted fertility and irrigation practices for *Anemone* plants. No chemical pest control measures were employed. Furthermore, no artificial light or photoperiodic treatments were given to the plants. Observation data was recorded in August of 2022.

Those skilled in the art will appreciate that certain characteristics will vary with older or, conversely, with younger plants. 'MACANE044' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, sixth edition, 2015.

A botanical description of 'MACANE044' and comparisons with the parents and most similar variety of common knowledge are provided below.

General plant description:

*Growth habit*.—Clumping herbaceous perennial with leaves developing from basal rosettes; flowering stems arising from the rosette also bear foliage; flowers are borne above the foliage; no lateral branching is present.

*Plant profile*.—Ovate.

*Growth rate*.—Moderate.

*Plant vigor*.—Moderate to high.

*Height*.—55.0 cm to the top of the foliar plane; approximately 70 to 80 cm to the top of the floral plane.

*Width*.—56.5 cm.

*Plant vigor*.—Moderately to highly vigorous.

*Propagation*.—Mode of propagation — Root cuttings. Time to produce a rooted cutting — Approximately 10 weeks to produce a rooted young plant. Time to produce flowering plant from rooted cutting — Approximately 12 months to produce a marketable potted plant.

*Pest resistance and susceptibility*.—Plants have not been observed to be susceptible or resistant to pathogens and pests common to *Anemone* sp.

*Environmental tolerances*.—Adapt to, at least, USDA Zones 4 to 9 and temperatures ranging from minus 30 degrees Celsius to 35 degrees Celsius; moderate tolerance to rain; moderate tolerance to wind.

Root system:

*Type*.—Moderately fibrous root system.

*Branching*.—Very freely branched.

*Density*.—Moderately dense.

*Distribution*.—Roots distributed evenly throughout the soil profile, from shallow to deep.

*Diameter*.—Largest roots measuring 0.5 mm in diameter.

*Texture*.—Smooth; lacking root hairs.

*Color*.—Greyed-brown, nearest to in between RHS N199C and N199D.

Foliage:

*Arrangement*.—Leaves are borne both basally and on the flowering stems; on stems.

*Basal leaves*.—Attachment — Petiolate. Arrangement — Alternate. Division — Trifoliate. Compound leaf outline — Ovate to near orbicular. Length — 14.0 cm, excluding the petiole. Width —15.6 cm. Attitude — Upward and outward, at an average angle of 60 degrees to horizontal. Leaflets — Shape — Ovate. Length — 10.1 cm. Width — 6.3 cm. Attitude — Outward, relative to the petiole. Aspect — Slightly to moderately carinate. Apex — Acute to apiculate. Base — Cuneate. Margin — Serrulate to incised. Texture, adaxial surface — Smooth, glabrous, and slightly glossy. Texture, abaxial surface — Smooth, glabrous, and matte. Color — Juvenile color, adaxial surface — Green, nearest to RHS 137B. Juvenile color, abaxial surface — Green, nearest to RHS 138B. Mature color, adaxial surface — Green, nearest to RHS 137B. Mature color, abaxial surface — Green, nearest to RHS 138B. Venation — Type — Laciniate. Vein color, adaxial surface — Yellow-green, nearest to RHS 144B. Vein color, abaxial surface — Yellow-green, nearest to RHS 144A. Stipules — General — Two leafy stipules present at the base of each leaf. Shape — Oblong to narrow ovate. Length — Average of 2.5 cm. Diameter — Average of 0.7 cm. Color, adaxial surface — Yellow-green, nearest to RHS 145B. Color, abaxial surface — Yellow-green, nearest to RHS 145B. Texture, adaxial surface — Smooth and glabrous. Texture, abaxial surface — Densely covered with short soft hairs; average length of hairs is 0.15 cm; colored translucent white, nearest to RHS NN155D. Petiole — Length — 16.4 cm. Diameter — 0.4 cm. Strength — Strong. Texture, adaxial and abaxial surfaces — Moderately covered with soft hairs; average length of hairs is 0.15 cm; colored translucent white, nearest to RHS NN155D. Luster, adaxial and abaxial surfaces — Very glossy. Color, adaxial surface — Yellow-green, nearest to RHS 144A. Color, abaxial surface — Yellow-green, nearest to RHS 144A.

*Cauline leaves*.—Attachment — Petiolate. Attitude — Upward and outward, at an average angle of 45 degrees to horizontal. Arrangement — Opposite. Division — Simple. Shape — Broadly ovate; trilobate; lobes are deeply lobed to near-cleft. Lobes — Depth of sinuses — Varying from deep to very deep. Sinus orientation — Divergent. Length — 10.7 cm. Width — 11.4 cm. Aspect — Slightly to moderately carinate. Apex — Acute to apiculate. Base — Cuneate. Margin — Serrate to incised. Texture, adaxial surface — Smooth, glabrous, and slightly glossy. Texture, abaxial surface — Smooth, glabrous, and matte. Color — Juvenile color, adaxial surface — Green, nearest to RHS 137B. Juvenile color, abaxial surface — Green, nearest to RHS 138B. Mature color, adaxial surface — Green, nearest to RHS 137B. Mature color, abaxial surface — Green, nearest to RHS 138B. Venation — Type — Laciniate. Vein color, adaxial surface — Yellow-green, nearest to RHS 144B. Vein color, abaxial surface — Yellow-green, nearest to RHS 144A. Stipules — General — Two leafy stipules present at the base of each leaf. Shape — Oblong to narrow ovate. Length — Average of 2.5 cm. Diameter — Average of 0.7 cm. Color, adaxial surface — Yellow-green, nearest to RHS 145B. Color, abaxial surface — Yellow-green, nearest to RHS 145B. Texture, adaxial surface — Smooth and glabrous. Texture, abaxial surface — Densely covered with short soft hairs; average length of hairs is 0.15 cm; colored translucent white, nearest to RHS NN155D. Petiole — Length — 1.4 cm. Diameter — 0.4 cm. Strength — Strong. Texture, adaxial and abaxial surfaces — Moderately covered with soft hairs; average length of hairs is 0.15 cm; colored translucent white, nearest to RHS NN155D. Luster, adaxial and abaxial surfaces — Very glossy. Color, adaxial surface — Yellow-green, nearest to RHS 144A. Color, abaxial surface — Yellow-green, nearest to RHS 144A.

Inflorescence:

*Habit*.—Cyme.

*Natural flowering season*.—Summer through late summer in Kirkcudbright, Scotland.

*Time to flower or response time*.—Approximately 10 months.

*Height*.—75.0 cm.

*Diameter*.—14.3 cm.

*Quantity of flowers per inflorescence*.—1, on average.

*Quantity of flowers per plant*.—10, on average.

*Quantity of flower buds per plant*.—200, on average.

*Quantity of flowers and flower buds per plant*.—210, on average.

*Peduncles*.—Length — Average of 41.4 cm. Diameter — Average of 0.5 cm. Angle — Average angle to soil level is approximately 80 degrees. Strength — Strong. Texture — Smooth. Pubescence — Moderately covered with soft hairs; average length of hairs is 1.0 mm; hairs colored greyed-white, nearest to RHS 156D. Luster — Moderately glossy. Color — Yellow-green, nearest to a mixture of RHS 144A and 146A; moderately to heavily suffused with a combination of greyed-purple, nearest to RHS N186C, and brown, nearest to RHS 200B.

Bud:

*Shape*.—Ovoid.

*Length*.—Average of 2.0 cm.

*Diameter*.—Ranging from 1.5 to 2.0 cm.

*Texture*.—Tomentose; hairs with an average length of 0.1 cm and colored greyed-white, nearest to in between RHS 156C and 156D.

*Luster*.—Matte.

*Color*.—Brown, RHS N200B; underside is suffused with yellow-green, nearest to RHS N144D.

Flower:

*Type and form*.—Rotate; single.

*Attitude*.—Upright to slightly outward; slightly pendulous at dusk.

*Flowering habit*.—Freely flowering.

*Flower longevity on plant*.—Approximately 10 days.

*Persistent or self-cleaning*.—Self-cleaning

*Fragrance*.—Non-fragrant.

*Width*.—Average of 6.2 cm high and 8.0 to 9.0 cm wide.

*Depth*.—Average of 1.6 cm.

*Tepals*.—Quantity — Average of 5. Arrangement — Rotate; the unfused tepals arranged in 2 whorls. Length — Varying from 4.0 to 4.5 cm. Width — 3.5 cm. Shape — Obovate. Apex — Obtuse. Base — Cuneate. Margin — Entire; slightly undulated. Texture, luster and pubescence of the upper surface — Glabrous, slightly glossy, and moderately velvety. Texture, luster and pubescence of the lower surface — Smooth, slightly glossy, and densely covered with appressed soft, silky hairs; average length of hairs is 0.75 mm; colored greyed-white, RHS 156D. Color — When opening, upper surface — White, nearest to in between RHS NN155B and NN155C, and fading to green-white towards the base, nearest to in between RHS 157B and 157C; central zone is heavily suffused with violet, RHS 84C; margined violet, nearest to a combination of RHS 85B and 85D. When opening, lower surface — White, nearest to RHS NN155A, and fading to green-white towards the base, nearest to RHS 157C; central zone is heavily suffused with violet, RHS 84C; margined violet, nearest to a combination of RHS 85B and 85D. Lower tepals are partially or entirely colored purple, nearest to RHS N77D, and suffused with yellow-green towards the base, RHS 147A. Fully opened, upper surface — White, nearest to RHS NN155D, and fading to green-white towards the base, nearest to RHS 157D; central zone is heavily suffused with violet, RHS 84C; margined violet, nearest to a combination of RHS 85B and 85D. Tepal color does not fade with age. Fully opened, lower surface — White, nearest to in between RHS NN155C and NN155D, and fading to green-white towards the base, nearest to RHS 157D; central zone is heavily suffused with violet, RHS 84C; margined violet, nearest to a combination of RHS 85A and 85D. Lower tepals are partially or entirely colored purple, nearest to RHS N79D, and suffused with yellow-green towards the base, nearest to RHS 147A. Tepal color does not fade with age. Tepal venation — Fully opened, upper surface — White, RHS NN155D, and fading to green-white towards the base, nearest to RHS 157D. Fully opened, lower surface — White, nearest to in between RHS NN155C and NN155D, and fading to green-white towards the base, nearest to RHS 157D. Lower tepals are partially or entirely colored purple, nearest to RHS N79D, and suffused with yellow-green towards the base, nearest to RHS 147A.

*Pedicels*.—Length — Average of 8.8 cm. Diameter — Average of 0.2 cm. Angle — Primary flowers at an angle of 0 degrees to peduncle axis; lateral flowers are at an average angle of 30 degrees to the peduncle axis. Strength — Moderately strong. Texture — Smooth. Pubescence — Densely covered with short soft hairs; average length of hairs is 0.75 mm; colored greyed-white, nearest to in between RHS 156C and 156D. Luster — Slightly glossy. Color — Yellow-green, nearest to RHS 148A; heavily suffused with brown, nearest to RHS 200A, where exposed to sunlight.

Reproductive organs:

*Stamens*.—Quantity — Approximately 230. Anthers — Shape — Oblong. Length — Approximately 1.5 mm.

Width — Approximately 0.75 mm. Color —Yellow-orange, RHS 17B. Filaments — Length — 8.0 mm, on average. Color — Yellow-green, nearest to RHS 150D. Pollen — Color — Yellow, RHS 11D. Quantity — None to sparse.

*Pistil*.—Quantity — 175, on average. Length — 1.0 mm. Style — Length — 0.5 mm. Color — Green, RHS 143C. Stigma — Shape — Club-shaped. Dimensions — 0.5 mm long and 0.5 cm in diameter. Color — Yellow-green, nearest to RHS N144D. Ovary Color — Yellow-green, RHS 144A.

Seed and fruit: Fruit and seeds have not been observed.

COMPARISONS WITH THE PARENT PLANTS

Plants of the new cultivar 'MACANE044' may be distinguished from its seed parent, *Anemone* 'Rosenschale' (unpatented), by the characteristics described in Table 1.

TABLE 1

| Characteristic | 'MACANE044' | 'Rosenschale' |
|---|---|---|
| Growth habit. | Clumping. | Spreading. |
| General coloration of the flower. | White, suffused with violet; the lower surface of the proximal tepals is partially or entirely colored purple. | White, suffused with red-purple. |
| Flowering season. | Longer than 'Rosenschale'. | Shorter than 'MACANE044'. |

Plants of the new cultivar 'MACANE044' differ from the pollen parent, an unnamed *Anemone* plant (unpatented), by the characteristics described in Table 2.

TABLE 2

| Characteristic | 'MACANE044' | Unnamed pollen parent |
|---|---|---|
| Plant height | Taller than the pollen parent. | Shorter than 'MACANE044'. |
| General coloration of the flower. | White, suffused with violet; the lower surface of the proximal tepals is partially or entirely colored purple. | White, and heavily suffused with lavender purple on the lower surface of the lower tepals. |

COMPARISONS WITH THE MOST SIMILAR VARIETY OF COMMON KNOWLEDGE

Plants of the new cultivar 'MACANE044' are most similar to the commercial variety, *Anemone* 'MACANE017' (U.S. Plant Pat. No. 30,496). A comparison of 'MACANE044' with 'MACANE017' is described in Table 3.

TABLE 3

| Characteristic | 'MACANE044' | 'MACANE017' |
|---|---|---|
| Plant height to the top of the floral plane. | Taller than 'MACANE017'. | Shorter than 'MACANE044' |
| General coloration of the flower. | White, suffused with violet; the lower surface of the proximal tepals is partially or entirely colored purple. | White with dark violet-blue reverse. |
| Flower size. | Larger than 'MACANE017'. | Smaller than 'MACANE044'. |

That which is claimed is:

1. A new and distinct variety of *Anemone* plant named 'MACANE044', substantially as described and illustrated herein.

* * * * *